United States Patent
Iwami et al.

(10) Patent No.: US 9,896,457 B2
(45) Date of Patent: Feb. 20, 2018

(54) MICROBIAL PRODUCT HAVING ANTIFUNGAL ACTIVITY

(71) Applicants: OP BIO FACTORY CO., LTD., Uruma-shi, Okinawa (JP); SEED RESEARCH INSTITUTE CO., LTD., Kunigami-gun, Okinawa (JP)

(72) Inventors: Morita Iwami, Okinawa (JP); Sachi Kato, Okinawa (JP); Yoshimi Matsumoto, Kizugawa (JP); Hideo Naoki, Sakai (JP)

(73) Assignees: OP Bio Factory Co., Ltd., Uruma (JP); Seed Research Institute Co., Ltd., Kunigami (JP)

(*) Notice: Subject to any disclaimer, the term of this patent is extended or adjusted under 35 U.S.C. 154(b) by 0 days.

(21) Appl. No.: 14/915,106

(22) PCT Filed: Aug. 29, 2014

(86) PCT No.: PCT/JP2014/072796
§ 371 (c)(1),
(2) Date: Feb. 26, 2016

(87) PCT Pub. No.: WO2015/030197
PCT Pub. Date: Mar. 5, 2015

(65) Prior Publication Data
US 2016/0207937 A1    Jul. 21, 2016

(30) Foreign Application Priority Data

Aug. 29, 2013  (JP) ................... 2013-178707

(51) Int. Cl.
| | | |
|---|---|---|
| *A61K 31/44* | (2006.01) | |
| *A01N 43/90* | (2006.01) | |
| *C07D 498/04* | (2006.01) | |
| *C12P 17/14* | (2006.01) | |
| *C12R 1/465* | (2006.01) | |

(52) U.S. Cl.
CPC .......... *C07D 498/04* (2013.01); *A01N 43/90* (2013.01); *C12P 17/14* (2013.01); *C12R 1/465* (2013.01)

(58) Field of Classification Search
CPC ....... C07D 498/04; A01N 43/90; C12P 17/14; C12P 14/14; C12R 1/465
See application file for complete search history.

(56) References Cited

FOREIGN PATENT DOCUMENTS

| JP | 60-156392 A | 8/1985 |
|---|---|---|
| JP | 01-199975 A | 8/1989 |

OTHER PUBLICATIONS

Shin et al (Bioorganic & Medicinal Chemistry Letters, 2006, 16, 5643-5645).*
Agena et al., "Kaiyo Biseibutsu Yurai no Saiboheki Gosei Sogai Kassei Busshitsu no Tansaku", Dai 15 Kai Japanese Society for Marine Biotechnology Taikai Koen Yoshishu, p. 110, abstract P-E-11 (Jun. 1, 2013).
Matsumoto et al., "A Novel Antifungal Agent Discovered from *Streptomyces* sp. in sea sand," ICAAC2013 poster presentation M-253c [retrieved from the internet at URL: http://www.opbio.com/topics/images/2013ICAACfinal.pdf (as uploaded on Sep. 20, 2013).
Shin et al., *Bioorg. Med. Chem. Letters*, 16: 5643-5645 (2006).
Japanese Patent Office, International Search Report in Japanese Patent Application No. PCT/JP2014/072796 (dated Dec. 2, 2014).

* cited by examiner

*Primary Examiner* — Kortney L Klinkel
*Assistant Examiner* — Ibrahim D Bori
(74) *Attorney, Agent, or Firm* — Leydig, Voit & Mayer, Ltd.

(57) ABSTRACT

Provided are a compound having a novel mother nucleus, which can be a promising drug discovery seed compound, use thereof as an antifungal agent, and a production method thereof and the like. A compound represented by the following formula:

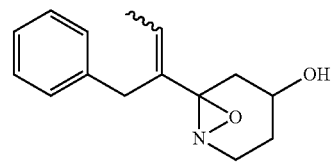

or a pharmaceutically acceptable salt thereof, and an antifungal agent containing same, and the like.

7 Claims, 2 Drawing Sheets

Fig. 1

|    | C ppm | H ppm      |     |
|----|-------|------------|-----|
| 1  | 47.8  | 3.22, 3.48 | CH2 |
| 2  | 28.8  | 1.22, 1.68 | CH2 |
| 3  | 62.5  | 3.80       | CH  |
| 4  | 36.5  | 2.00, 2.35 | CH2 |
| 5  | 84.7  |            | C   |
| 6  | 139.3 |            | C   |
| 7  | 33.1  | 3.43, 3.54 | CH2 |
| 8  | 140.9 |            | C   |
| 9  | 129.7 | 7.19       | CH  |
| 10 | 129.3 | 7.24       | CH  |
| 11 | 127.0 | 7.14       | CH  |
| 12 | 129.3 | 7.24       | CH  |
| 13 | 129.7 | 7.19       | CH  |
| 14 | 126.3 | 5.91       | CH  |
| 15 | 13.7  | 1.69       | CH3 |
| 16 |       | 4.59       | OH  |

Fig. 2

| | strain name | | KKRM | MCFG | AMPH | 5-FC | FLCZ | ITCZ | VRCZ | MCZ | culture time |
|---|---|---|---|---|---|---|---|---|---|---|---|
| 1 | Candida albicans | ATCC24433 | 0.5 | ≤0.015 | 1 | 0.25 | 0.25 | ≤0.015 | ≤0.015 | ≤0.03 | 24 hr |
| 2 | Candida albicans | ATCC90028 | 0.125 | 0.015 | 0.25 | ≤0.125 | ≤0.125 | ≤0.015 | ≤0.015 | ≤0.03 | |
| 3 | Candida albicans | ATCC90029 | 0.125 | 0.015 | 0.125 | >64 | 0.25 | ≤0.015 | ≤0.015 | ≤0.03 | |
| 4 | Candida parapsilosis | ATCC22019 | 0.015 | 0.5 | 0.25 | ≤0.125 | 0.25 | ≤0.015 | ≤0.015 | 0.06 | |
| 5 | Candida parapsilosis | ATCC90018 | 0.5 | ≤0.015 | 0.125 | ≤0.125 | 0.5 | ≤0.015 | ≤0.015 | ≤0.03 | |
| 6 | Candida tropicalis | ATCC750 | >8 | 0.06 | 0.25 | 4 | 1 | 0.06 | 0.03 | 0.5 | |
| 7 | Candida krusei | ATCC6258 | 0.125 | 0.03 | 0.5 | ≤0.125 | 32 | 1 | 0.25 | 1 | |
| 8 | Candida glabrata | ATCC90030 | 1 | | 0.5 | 1 | 8 | 1 | 0.25 | 0.125 | |
| 9 | Candida guilliermondii | clinical isolate | 0.5 | 1 | 0.25 | 0.25 | 4 | 0.25 | 0.06 | 0.25 | |
| 10 | Candida lusitaniae | clinical isolate | 0.5 | 0.125 | 1 | 0.25 | 0.25 | 0.06 | ≤0.015 | 0.06 | |
| 11 | Aspergillus fumigatus | clinical isolate | 2 | ≤0.015 | 1 | 64 | >64 | 0.125 | 0.25 | 0.5 | 48 hr |
| 12 | Aspergillus flavus | clinical isolate | 4 | ≤0.015 | 1 | 4 | 32 | 0.125 | 0.25 | 2 | |
| 13 | Aspergillus niger | clinical isolate | 8 | ≤0.015 | 0.5 | 0.5 | >64 | 0.25 | 0.125 | 1 | |
| 14 | Aspergillus terreus | clinical isolate | 0.25 | ≤0.015 | 0.5 | 0.25 | 16 | ≤0.015 | 0.03 | 0.06 | |

MICROBIAL PRODUCT HAVING ANTIFUNGAL ACTIVITY

CROSS-REFERENCE TO RELATED APPLICATIONS

This patent application is the U.S. national phase of International Patent Application No. PCT/JP2014/072796, filed Aug. 29, 2014, which claims the benefit of Japanese Patent Application No. 2013-178707, filed on Aug. 29, 2013, which are incorporated by reference in their entireties herein.

TECHNICAL FIELD

The present invention relates to a compound having a novel mother nucleus, use thereof as an antifungal agent, and a production method thereof, and the like.

BACKGROUND ART

In recent years, along with an increase in elderly people, progress of advanced medicine, immunodeficiency of late stage cancer patients and the like, infections with fungi have been increasing. These infections provide serious effects, often causing death. Since there are not many kinds of existing antifungal agents, and their toxicity is high, the mother nucleus of a new antifungal agent, which is different from that of conventional medicaments, has been desired. In addition, since the use of antifungal agents causes increased emergence of resistant bacteria, the development of a new medicament has been earnestly desired. While candin-based antifungal agents show low toxicity, since the molecular weight thereof is large, reactivity with serum poses problems. Azole-based antifungal agents have a problem in that administration at a high concentration is difficult in view of the toxicity thereof. Therefore, an effective, low-molecular-weight compound showing low reactivity with serum and low toxicity has been strongly desired.

Conventionally, in search of a pharmaceutical product seed compound from microbial metabolites, terrestrial separation sources have been mainly harvested and subjected to microorganism separation. The microbial metabolites found to date include penicillin and adriamycin, and a number of antibiotics and anticancer agents were found and utilized as therapeutic drugs for infection, cancer and the like. However, due to the continuous search over a long term, microbial metabolites obtained from the land areas are mostly known compounds, and a secondary metabolite to be a candidate for a novel medicament is extremely difficult to obtain. Consequently, the development of a novel medicament by natural substance drug discovery corporations was rapidly reduced. To overcome the situation, screening using a chemical library (natural substance and synthesized compound) has been conducted on a global scale. Unexpectedly, however, a promising novel medicament candidate compound was not obtained from the chemical library. Under such circumstances, it is extremely difficult to obtain a new medicament candidate compound.

SUMMARY OF THE INVENTION

Problems to be Solved by the Invention

The present invention has been made in view of the aforementioned situation in the technical field, and aims to provide a compound having a novel mother nucleus, which can be a promising drug discovery seed compound, use thereof as an antifungal agent, and a production method thereof and the like.

Means of Solving the Problems

In view of the aforementioned current situation in the search of a novel medicament candidate compound, the present inventors took note of the marine microorganism resources. Marine microorganism resources have been scarcely utilized, and have a high possibility of affording a novel secondary metabolite. However, a special technique is necessary for harvesting separation sources, and the culture technique therefor has not been sufficiently established. The present inventors have conducted intensive studies of a method of collecting samples from the ocean, a culture method and an evaluation method of microorganism, and the like and succeeded in isolating a promising microorganism strain for the development of an antifungal agent. The 16S ribosome base sequence analysis has revealed that the microorganism strain is actinomycetes of the genus *Streptomyces*. Furthermore, they have successfully isolated and purified a compound showing activity from a culture medium of the microorganism. The compound had a small molecular weight, low reactivity with serum, and a strong antifungal action. As a result of structural analyses, moreover, the compound was found to have a novel mother nucleus, and to be promising as a seed compound for the development of a novel medicament. The present inventors conducted further studies based on these findings and completed the present invention.

Accordingly, the present invention is as described below.
[1] A compound represented by the following formula:

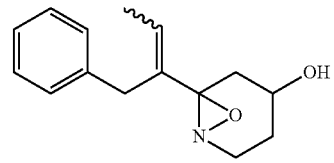

or a pharmaceutically acceptable salt thereof.
[2] A compound showing the following $^{13}$C-NMR and $^{1}$H-NMR spectra measured using deuterated methanol as a measurement solvent:

TABLE 1

| | C ppm | H ppm | |
|---|---|---|---|
| 1 | 47.8 | 3.22, 3.48 | CH2 |
| 2 | 28.8 | 1.22, 1.68 | CH2 |
| 3 | 62.5 | 3.80 | CH |
| 4 | 36.5 | 2.00, 2.35 | CH2 |
| 5 | 84.7 | | C |
| 6 | 139.3 | | C |
| 7 | 33.1 | 3.43, 3.54 | CH2 |
| 8 | 140.9 | | C |
| 9 | 129.7 | 7.19 | CH |
| 10 | 129.3 | 7.24 | CH |
| 11 | 127.0 | 7.14 | CH |
| 12 | 129.3 | 7.24 | CH |
| 13 | 129.7 | 7.19 | CH |
| 14 | 126.3 | 5.91 | CH |
| 15 | 13.7 | 1.69 | CH3 |
| 16 | | 4.59 | OH | or a pharmaceutically acceptable salt thereof.

[3] A medicament or pesticide comprising the compound of the above-mentioned [1] or [2], or a pharmaceutically acceptable salt thereof.
[4] The medicament or pesticide of the above-mentioned [3], which is an antifungal agent.
[5] The medicament or pesticide of the above-mentioned [4], targeting a fungus of the genus selected from the group consisting of the genus *Candida* and the genus *Aspergillus*.
[6] A production method of the compound of the above-mentioned [1] or [2] or a pharmaceutically acceptable salt thereof, comprising culturing a bacterium of the genus *Streptomyces* under accession No. NITE BP-01677 or a variant thereof in a medium containing a carbon source to produce the compound or a pharmaceutically acceptable salt thereof in the medium, and recovering the compound or a pharmaceutically acceptable salt thereof from the culture.
[7] A bacterium of the genus *Streptomyces* under accession No. NITE BP-01677 or a variant thereof.
The present invention also provides the following.
[8] A method for the prophylaxis or treatment of mycosis in a mammal, comprising administering an effective amount of the compound of the above-mentioned [1] or [2], or a pharmaceutically acceptable salt thereof to the mammal in need thereof.
[9] A method of controlling a plant disease, comprising treating the target crop and/or a seed of the target crop with an effective amount of the compound of the above-mentioned [1] or [2] or a pharmaceutically acceptable salt thereof.
[10] The compound of the above-mentioned [1] or [2] or a pharmaceutically acceptable salt thereof for use for the prophylaxis or treatment of mycosis in a mammal.

Effect of the Invention

Since the compound of the present invention has a small molecular weight, low reactivity with serum, and a strong antifungal action, it is useful as an antifungal agent. Also, since the compound of the present invention has a novel mother nucleus, it is promising as a seed compound for the development of a novel medicament. The present invention also provides a production method of the compound of the present invention.

BRIEF DESCRIPTION OF THE DRAWINGS

FIG. 1 shows the results of the NMR analysis of the compound of the present invention.
FIG. 2 shows the results (MIC (µg/mL)) of the antifungal agent sensitivity test, wherein KKRM is the compound of the present invention, MCFG is Micafungin, AMPH is amphotericin B, 5-FC is flucytosine, FLCZ is fluconazole, ITCZ is itraconazole, VRCZ is Voriconazole, and MCZ is miconazole.

DESCRIPTION OF EMBODIMENTS

The present invention is explained in detail below.
The present invention provides a compound represented by the following formula:

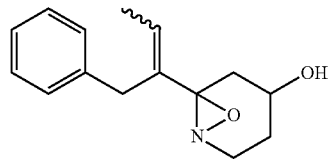

or a pharmaceutically acceptable salt thereof (hereinafter these are to be generically referred to as the compound of the present invention). While the compound of the present invention can contain one or more kinds of isomers such as an optical isomer based on an asymmetric carbon atom, a geometric isomer based on a double bond and the like, all of such isomers and mixtures thereof are encompassed in the scope of the present invention. In the above-mentioned formula, a wavy line adjacent to the double bond moiety intends to encompass both of the following two kinds of geometric isomers.

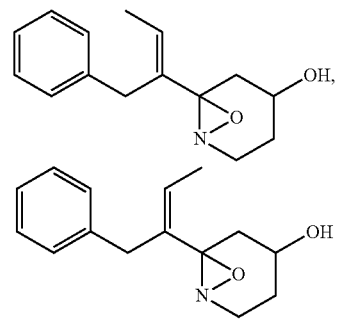

Examples of the pharmaceutically acceptable salt include salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like.

The compound of the present invention can be produced using a bacterium of the genus *Streptomyces* isolated by the present inventors from the sea sand in Kakeroma Island, Kagoshima Prefecture (hereinafter to be also referred to as the bacterium of the present invention) or a variant thereof. The bacterium was deposited in the National Institute of Technology and Evaluation (NITE) Patent Microorganisms Depositary, Kazusa-kamatari, Kisarazu, Chiba 2-5-8, Japan (accession No.: NITE P-1677, deposit date: Aug. 1, 2013), a request for transfer of NITE P-01677 to the deposit based on the Budapest Treaty was filed, and the request was received on Jul. 30, 2014 (transfer date), and the bacterium is internationally deposited under accession No.: NITE BP-01677.

The bacterium has aerial hypha in a grayish color, and a spore chain with a shorter helical form. The soluble dye produces yellowish pigment. The color of the backside is cream to pale-yellow. The matured spores form a spore mass.

The variant is a strain derived from the bacterium of the present invention, and is not particularly limited as long as it can produce the compound of the present invention. For example, the nucleotide sequence of the 16S rRNA gene of the variant is the same as the nucleotide sequence of the 16S rRNA gene of the bacterium of the present invention (i.e., 100% identical) or substantially the same (e.g., when produced by mutation in the presence of a mutagenic substance and the like as mentioned below). The variant also shows morphological, physiological characteristics similar to those of the bacterium of the present invention.

When used in the present specification, a nucleotide sequence "substantially the same as the nucleotide sequence of the 16S rRNA gene of the bacterium of the present invention" means that the nucleotide sequence to be compared has at least 99%, preferably not less than 99.1%, more preferably not less than 99.2%, further preferably not less than about 99.5%, nucleotide sequence identity. The identity of the nucleotide sequence can be determined by a method known per se and, for example, calculated using homology calculation algorithm NCBI BLAST (National Center for Biotechnology Information Basic Local Alignment Search Tool) under the following conditions (expectancy=10; gap allowed; filtering=ON; match score=1; mismatch score=−3).

The variant can be produced, for example, by a modification operation of the bacterium of the present invention. Examples of the modification operation include mutation in the presence of a mutagenic substance and the like, introduction of a gene capable of increasing the usefulness of the bacterium of the present invention (e.g., gene that increases producibility of the compound of the present invention), and destruction of the gene carried by the bacterium of the present invention, and a combination of these operations and the like.

The bacterium of the present invention or a variant thereof can be maintained and grown by culturing in a nutrition medium containing a carbon source. Examples of the carbon source include saccharides (e.g., monosaccharides such as glucose, galactose and the like, disaccharides such as sucrose and the like, polysaccharides such as starch and the like), glycerol and the like, preferably starch. The nutrition medium preferably also contains a nitrogen source, and examples of the nitrogen source include casitone, yeast extract, meat extract, malt extract and the like. Addition of $NaH_2PO_4$ to the medium can promote early production of the compound of the present invention. Furthermore, the medium preferably contains sea water, and the concentration thereof is about 10%-40% of the concentration of general sea water (i.e., artificial sea water 38.4 g/L). Therefore, the artificial sea water concentration of the medium is, for example, 0.384 g/L-38.4 g/L, preferably 1.92 g/L-13.04 g/L, more preferably 3.84 g/L-15.36 g/L. Examples of the salt content include sodium chloride, magnesium chloride, magnesium sulfate, calcium sulfate, potassium chloride and the like. An exemplary composition of the medium may be starch 4%, meat extract 0.4%, casitone 0.4%, $NaH_2PO_4$ 0.1%, and may be a liquid medium with 10% of the general sea water concentration. Other culture conditions are: stirring culture at pH 6.8-7.5 (e.g., 7.0), 25-35° C. (e.g., 28° C.).

The compound of the present invention can be produced in a culture broth obtained by culturing the bacterium of the present invention or a variant thereof under the aforementioned culture conditions for, for example, 2-14 days. The compound of the present invention can be recovered from the culture, and preferably isolated and purified. Isolation and purification can be performed by a method well known in the technical field. For example, concentration, extraction, chromatography, reprecipitation, recrystallization and the like can be used.

As shown in the below-mentioned Examples, the compound of the present invention has strong antifungal activity against a broad range of fungi. Therefore, the compound of the present invention is useful as, for example, an antifungal agent. Therefore, the present invention also provides an antifungal agent containing the compound of the present invention as an active ingredient (hereinafter to be also referred to as the antifungal agent of the present invention). The antifungal agent of the present invention can be used as a medicament or pesticide.

Examples of the fungi to be the target of the antifungal agent of the present invention include, but are not limited to, fungi such as the genus *Candida* (e.g., *Candida albicans, Candida parapsilosis, Candida tropicalis, Candida krusei, Candida glabrata, Candida quilliermondii, Candida lusitaniae* etc.), the genus *Aspergillus* (e.g., *Aspergillus fumigatus, Aspergillus flavus, Aspergillus niger, Aspergillus terreus* etc.), the genus *Trichophyton* (e.g., *Trichophyton rubrum, Trichophyton mentagrophytes, Trichophyton tonsurans, Microsporum canis, Microsporum gypseum, Trichophyton verrucosum* etc.) and the like. Mycosis is not particularly limited, and deep skin mycosis, deep mycosis, mycetoma, and fungemia can be mentioned.

When the antifungal agent of the present invention is used as a pesticide, the target crop is not particularly limited and, for example, plants such as grain (e.g., rice, barley, wheat, rye, oats, corn, kaoliang etc.), beans (soybean, adzuki bean, broad bean, pea, peanut etc.), fruit-tree, fruits (apple, citrus, pear, grapes, peach, ume (Japanese plum), cherry, walnut, almond, banana, strawberry etc.), vegetables (cabbage, tomato, spinach, broccoli, lettuce, onion, green onion, bell pepper etc.), root vegetables (carrot, potato, sweet potato, radish, lotus root, turnip etc.), crops for processing (cotton, hemp, kozo (paper mulberry), mitsumata plant, rape seed, beet, hop, sugarcane, sugar beet, olive, rubber, coffee, tobacco, tea etc.), gourds (pumpkin, cucumber, watermelon, melon etc.), grasses (orchard grass, sorghum, timothy, clover, alfalfa etc.), sods (Korean lawn grass, bentgrass etc.), crops for flavor etc. (lavender, rosemary, thyme, parsley, pepper, ginger etc.), flowering plants (*chrysanthemum*, rose, orchid etc.) and the like can be mentioned. The antifungal agent of the present invention can be used for controlling the diseases related to the aforementioned fungi in the crops, by treating the target crop and/or seed of the target crop with an effective amount thereof.

The pesticide can be used in the following form, and generally used together with an adjuvant conventionally used in the pharmaceutical fields. The compound of the present invention is formulated by a known method into, for example, emulsion stock solution, sprayable paste, sprayable or dilutable solution, dilutable emulsion, wettable agent, water soluble powder, powder, granule, flowable pesticide, dry flowable pesticide, smoking agent, fumigant and, for example, capsule made of a polymer substance.

As additive and carrier when the object is a solid agent, plant-derived powder such as soy flour, wheat flour and the like, mineral fine powder such as diatomaceous earth, apatite, plaster, talc, bentonite, clay and the like, and organic and inorganic compounds such as sodium benzoate, urea, salt cake and the like can be used.

When a liquid dosage form is desired, aromatic hydrocarbons such as vegetable oil, mineral oil, kerosene, xylene and toluene, amides such as formamide, and dimethylformamide, sulfoxides such as dimethyl sulfoxide, ketones such as methyl isobutyl ketone and acetone, trichloroethylene, water and the like are used as solvents. To afford these preparations in a uniform and stable form, a surfactant can also be added where necessary. The thus-obtained wettable agent, emulsion, aqueous solution, flowable pesticide, and dry flowable pesticide are diluted with water to a given concentration and used as a suspension or emulsion, and powder and granule are used by directly spraying on the soil or plant.

The content and dose of the active ingredient in a pesticide containing the compound of the present invention can be changed in a wide range depending on the dosage form, the kind of fungi to be the application target, target crop and the like.

On the other hand, when the antifungal agent of the present invention is used as a medicament, it can be administered to a treatment target, for example, a mammal (e.g., human, mouse, rat, hamster, rabbit, cat, dog, bovine, sheep, monkey etc.) by an oral or parenteral administration route (e.g., intravenous injection, intramuscular injection, subcutaneous administration, rectal administration, transdermal administration).

When the antifungal agent of the present invention is transdermally administered, it can contain, besides the above-mentioned active ingredient, oily base, emulsifier and emulsion stabilizer, solubilizing agents, powder component, polymer component, adhesiveness improver, film-forming agent, pH adjuster, antioxidant, antiseptic agent, preservative, shape retention agent, moisturizer, skin protector, algefacient, flavor, colorant, chelating agent, lubricant, blood circulation promoter, astringent, tissue repair promoter, adiaphoretic, plant extraction component, animal extraction component, anti-inflammatory agent, antipruritic agent and the like as necessary. As these additives, those generally used for preparations can be used.

The antifungal agent of the present invention can be used by formulating the above-mentioned components other than the active ingredient and the like into external drugs such as cream, liquid, lotion, emulsion, tincture, ointment, aqueous gel, oily gel, aerosol, powder, shampoo, soap, enamel agent for application to nail and the like, by a method conventionally used in the field of pharmaceutical preparations.

When the antifungal agent of the present invention is orally administered, it can be prepared into a dosage form suitable for oral administration such as capsule, tablet, granule, powder, pill, fine granules, troche and the like. These preparations can be produced using additives generally used for oral preparations, such as excipient, filler, binder, moistening agent, disintegrant, surfactant, lubricant, dispersing agent, buffering agent, preservative, solubilizing agent, antiseptic agent, flavoring agent, soothing agent, stabilizer and the like by a conventional method.

The present invention is explained in more detail in the following by referring to Examples, which are not to be construed as limitative.

EXAMPLES

Example 1: Isolation and Analysis of *Streptomyces* sp. A84 Strain

A separation source was collected from the sea sand of Kakeroma Island, Kagoshima Prefecture. The strain was isolated from the collected sample, and the isolated microorganism strain was applied to evaluation screening using antifungal activity as an index. As a result, a promising strain was obtained, which was further examined carefully.

The strain was analyzed by the phylogenetic classification method of 16S rRNA to find that the producing microorganism is actinomycetes of the genus *Streptomyces*, and the related species are *Streptomyces nodosus* (98.8% homology) and *Streptomyces glomeratus* (99.0% homology). The homology of the base sequence with the most related *Streptomyces glomeratus* was 99.0%, which suggests the possibility of a new species. This strain was named *Streptomyces* sp. A84 strain. *Streptomyces* sp. A84 strain was deposited in the National Institute of Technology and Evaluation (NITE) Patent Microorganisms Depositary, Kazusakamatari, Kisarazu, Chiba 2-5-8, Japan (accession No.: P-01677, deposit date: Aug. 1, 2013), a request for transfer of NITE P-01677 to the deposit based on the Budapest Treaty was filed, and the request was received on Jul. 30, 2014 (transfer date), and the bacterium is internationally deposited under accession No.: NITE BP-01677.

Example 2: Study of Production Medium for A84 Strain

A production medium for A84 strain was studied.
As a result of the study of the medium, the following medium showed good productivity.
medium composition:
starch 4%
casitone 0.1%
$NaH_2PO_4$ 0.1%
artificial sea water (MARINE ART SUPER FORMULA 1, manufactured by Tomita Pharmaceutical Co., Ltd.) 0.384%
pH 7.0
Under culture conditions, the medium (100 ml) was filled in a 300 ml Erlenmeyer flask and the strain was cultured at 28° C., 200 rpm for 2-4 days.

Example 3: Separation, Purification and Analysis of Active Ingredient

A84 strain was inoculated to a medium (100 ml) having the composition described in Example 2 in a 300 ml Erlenmeyer flask, and cultured at 28° C., 200 rpm (rotary shaker) for 3 days. The solvent was extracted from the culture medium by using an equal amount of ethyl acetate, and ethyl acetate was evaporated. The dried sample was dissolved in a small amount of methanol, and separated and purified by column chromatography (HPLC) using an ODS column (purity not less than 95%, 100 µg/1 L).

LC/MS analysis, NMR analysis, and optical rotation measurement of the active ingredient were performed. The measurement conditions were as described below.
LC/MS:
  apparatus: model number Agilent6540
  ion source: AJS-ESI, ESI, APC1
NMR:
  apparatus: ECA-600 (manufactured by JEOL Ltd.)
  magnet: SCM 14.olT
  bore diameter: 54 mm
  probe: 3 mm, 5 mm, 10 mm
  measurement solvent: deuterated methanol optical rotation:
  polarimeter: P-1030 (manufactured by JASCO Corporation)
  solvent: methanol (for HPLC)
  sample concentration: 4 mg/ml
  temperature: 28
  cell: 3.5 mm×10.0 mmϕ, cylindrical glass cell (mod.CG3-10)
  λ: 589 nm As a result, the molecular formula was determined to be $C_{15}H_{19}NO_2$, and the molecular weight was 245.1416, and the NMR spectrum was determined to be as shown in FIG. 1. The specific optical rotation was −3.25000 deg (Avg), and the optical rotation was −0.0013 deg (Avg).

Experimental Example 1: Measurement of Antifungal Activity

Minimum inhibitory concentration (MIC) was measured by the trace liquid dilution method. The measurement was performed using yeast-like fungi FP 'Eiken' (Eiken Chemical Co., Ltd.) and according to the manual of the product.

MIC (μg/mL) of various medicaments to each species is shown in FIG. 2. The active ingredient of the present invention showed good activity on *Candida* spp. and *Aspergillus* spp.

INDUSTRIAL APPLICABILITY

Since the compound of the present invention has a small molecular weight, low reactivity with serum, and a strong antifungal action, it is useful as an antifungal agent. Also, since the compound of the present invention has a novel mother nucleus, it is promising as a seed compound for the development of a novel medicament. The present invention also provides a production method of the compound of the present invention.

This application is based on patent application No. 2013-178707 filed in Japan (filing date: Aug. 29, 2013), the contents of which are encompassed in full herein.

The invention claimed is:

1. A composition comprising a compound represented by the following formula:

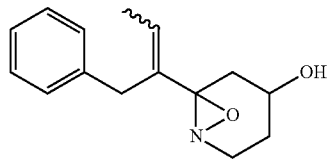

or a pharmaceutically acceptable salt thereof, wherein the composition is formulated as an emulsion stock solution, a sprayable paste, a sprayable or dilutable solution, a dilutable emulsion, a wettable agent, a powder, a granule, a smoking agent, a fumigant, or a capsule.

2. The composition of claim 1, wherein the composition is suitable for oral administration.

3. The composition of claim 1, wherein the composition is a capsule, tablet, granule, powder, pill, fine granules, or troche.

4. The composition of claim 1, wherein the composition is suitable for parenteral administration.

5. The composition of claim 1, wherein the composition is a cream, liquid, lotion, emulsion, tincture, ointment, aqueous gel, oily gel, aerosol, powder, shampoo, soap, or enamel agent.

6. A method for the treatment of mycosis in a mammal, comprising administering an effective amount of the compound of claim 1 or a pharmaceutically acceptable salt thereof to the mammal in need thereof.

7. A production method of the compound represented by the following formula:

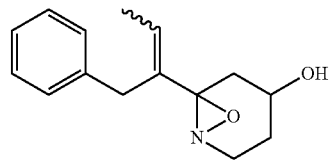

or a pharmaceutically acceptable salt thereof, comprising culturing a bacterium of the genus *Streptomyces* under accession No. NITE BP-01677 or a variant thereof in a medium containing a carbon source to produce the compound or a pharmaceutically acceptable salt thereof in the medium, and recovering the compound or a pharmaceutically acceptable salt thereof from the culture.

* * * * *